United States Patent
Johnston et al.

(10) Patent No.: US 9,612,188 B2
(45) Date of Patent: Apr. 4, 2017

(54) METHOD FOR MONITORING AND PURIFYING AIR

(71) Applicant: Alen Corporation, Austin, TX (US)

(72) Inventors: Luke Johnston, Austin, TX (US); Mark Vander Berg, Austin, TX (US); Suppawat Kosumsuppamala, Austin, TX (US); Jason Matocha, Pflugerville, TX (US)

(73) Assignee: Alen Corporation, Austin, TX (US)

( * ) Notice: Subject to any disclaimer, the term of this patent is extended or adjusted under 35 U.S.C. 154(b) by 197 days.

(21) Appl. No.: 14/730,342

(22) Filed: Jun. 4, 2015

(65) Prior Publication Data

US 2015/0355069 A1    Dec. 10, 2015

Related U.S. Application Data

(60) Provisional application No. 62/007,959, filed on Jun. 5, 2014.

(51) Int. Cl.
   *G01N 15/10*     (2006.01)
   *G01N 33/00*     (2006.01)
   *F24F 11/00*     (2006.01)

(52) U.S. Cl.
   CPC .......... *G01N 15/10* (2013.01); *F24F 11/0017* (2013.01); *G01N 33/0036* (2013.01); *Y02B 30/78* (2013.01)

(58) Field of Classification Search
   CPC ........ B01D 46/442; F24F 3/16; F24F 3/1603; F24F 3/166; F24F 11/0017; F24F 11/0078; F24F 11/0079; F24F 11/04; Y02B 30/746; G01N 15/10; G01N 33/0036
   USPC ............. 73/31.01–31.07; 422/108, 121, 122; 454/75; 700/276
   See application file for complete search history.

(56) References Cited

U.S. PATENT DOCUMENTS

| | | | |
|---|---|---|---|
| 2005/0144963 A1* | 7/2005 | Peterson | F24F 11/0001 62/178 |
| 2010/0037679 A1* | 2/2010 | Niezgoda | B01D 46/0038 73/31.02 |

* cited by examiner

*Primary Examiner* — Laura Martin
*Assistant Examiner* — Irving A Campbell
(74) *Attorney, Agent, or Firm* — DuBois, Bryant & Campbell, LLP; William D. Wiese

(57) ABSTRACT

An air purifier is presented with a sensor controlling a motorized fan, wherein the sensor continuously and automatically adjusts the sensitivity setting of the sensor as the quality of air being purified changes. The average air quality readings of the air passing through an air purifier are monitored over a designated time period and, as the quality fluctuates, the sensitivity of the sensor is automatically adjusted. If the air quality is poor (i.e. a high particulate count), the sensitivity of the sensor will be adjusted to a less sensitive setting (i.e. allowing higher fan speeds so that more air can be moved through the filter) and, if the air quality is good (i.e. a low particulate count), the sensitivity of the sensor will be adjusted to a more sensitive setting (i.e. setting a lower maximum fan speed because not as much air needs to move through the filter).

12 Claims, 5 Drawing Sheets

| Sensitivity Setting | Part. Level | Fan Speed | Part. Level (pcs/283ml=0.01 ft³) | Fan Speed | Part. Level (pcs/283ml=0.01 ft³) | Fan Speed | Part. Level (pcs/283ml=0.01 ft³) | Fan Speed |
|---|---|---|---|---|---|---|---|---|
| 1 | 0 | Low | 10 | Medium | 40 | High | 100 | Turbo |
| 2 | 0 | Low | 30 | Medium | 100 | High | 250 | Turbo |
| 3 | 0 | Low | 100 | Medium | 250 | High | 750 | Turbo |
| 4 | 0 | Low | 250 | Medium | 750 | High | 1000 | Turbo |
| 5 | 0 | Low | 750 | Medium | 1000 | High | 1250 | Turbo |
| 6 | 0 | Low | 1000 | Medium | 1500 | High | 2000 | Turbo |
| 7 | 0 | Low | 1500 | Medium | 2500 | High | 3000 | Turbo |

| Sensitivity Setting | Part. Level | Fan Speed | Part. Level (pcs/283ml=0.01 ft$^3$) | Fan Speed | Part. Level (pcs/283ml=0.01 ft$^3$) | Fan Speed | Part. Level (pcs/283ml=0.01 ft$^3$) | Fan Speed |
|---|---|---|---|---|---|---|---|---|
| 1 | 0 | Low | 10 | Medium | 40 | High | 100 | Turbo |
| 2 | 0 | Low | 30 | Medium | 100 | High | 250 | Turbo |
| 3 | 0 | Low | 100 | Medium | 250 | High | 750 | Turbo |
| 4 | 0 | Low | 250 | Medium | 750 | High | 1000 | Turbo |
| 5 | 0 | Low | 750 | Medium | 1000 | High | 1250 | Turbo |
| 6 | 0 | Low | 1000 | Medium | 1500 | High | 2000 | Turbo |
| 7 | 0 | Low | 1500 | Medium | 2500 | High | 3000 | Turbo |

*FIG. 1*

Sensitivity Setting v. Particulate Level

| 1 | 2 | 3 | 4 | 5 | 6 | 7 |
|---|---|---|---|---|---|---|
|   |   |   |   |   |   | 3000 |
|   |   |   |   |   | 2000 | 2500 |
|   |   |   |   | 1250 | 1500 | 1500 |
|   |   |   | 1000 | 1000 | 1000 |   |
|   |   | 750 | 750 | 750 |   |   |
|   | 250 | 250 | 250 |   |   |   |
| 100 | 100 | 100 |   |   |   |   |
| 40 | 30 |   |   |   |   |   |
| 10 |   |   |   |   |   |   |

FIG. 4

| Sensitivity Setting | Part. Level (pcs/283ml) | Avg. Particle Reading | Part. Level (pcs/283ml) |
|---|---|---|---|
| 1 | 0< | X | <=40 |
| 2 | 40< | X | <=100 |
| 3 | 100< | X | <=250 |
| 4 | 250< | X | <=750 |
| 5 | 750< | X | <=1000 |
| 6 | 1000< | X | <=1500 |
| 7 | 1500< | X |   |

FIG. 5

METHOD FOR MONITORING AND PURIFYING AIR

PRIORITY STATEMENT UNDER 35 U.S.C. §119

This application claims priority under 35 U.S.C. §119 based upon prior U.S. Provisional Patent Application Ser. No. 62/007,959, filed Jun. 5, 2014, in the name of Alen Corporation, entitled "IMPROVED METHOD FOR MONITORING AND PURIFYING AIR," the disclosure of which is incorporated herein in its entirety by this reference.

BACKGROUND OF THE INVENTION

Air purifiers with built in particle sensors usually only have three to five fan speeds and a control system that is programmed to recognize only one sensor sensitivity setting. Depending on which country or region you are in, this sensor sensitivity setting may or may not be appropriate to keep your unit operating optimally.

For example, air in China can contain, on average, ten to twenty times more contaminants than air in the United States. An air purifier can be configured with a control system that is programmed to be less sensitive in this environment so that the air purifier will operate at its maximum level (i.e. the highest fan speed) when air is relatively dirty by China standards and will then operate at its minimum level (i.e. the lowest fan speed) when the air is relatively clean by China standards. However, if that same unit was operated in the United States where the air includes relatively less particulate, the control system would consider even the dirtiest air to be clean, and the unit would always either be off or operate at its lowest setting.

By contrast, if the control system in an air purifier is programmed to be more sensitive, the air purifier will operate at its maximum level (i.e. the highest fan speed) when air is relatively dirty by United States standards and then operate at its minimum level (i.e. the lowest fan speed or off) when the air is relatively clean by United States standards. However, if that same unit was operated in China where the air contains more particulate, the control system would consider even the cleanest air to be dirty, and the unit would always operate at its highest setting.

Some air purifiers are configured to visually indicate when the air is clean (for example by displaying a green light) or when the air is dirty (for example by displaying a red light). In addition, some air purifiers are configured to allow the control system to adjust the sensitivity of the sensor. Therefore, instead of having a sensor with only one sensitivity level which results in an absolute measurement for "clean air" and an absolute measurement for "dirty air," there are a number of different sensitivity levels that may be adjusted by the user to cover the entire spectrum of air quality levels.

However, having multiple sensor sensitivities does not resolve the problem described above because, even if the user is allowed to adjust the sensitivity level of the sensor, the quality of the air fluctuates over time. Therefore, if a user adjusts the sensitivity of the sensor at one time and the air quality changes over the next day, hour or week, the user would need to continuously adjust the sensitivity as the quality of the air changed.

It is desirable, therefore, to have an air purifier having a control system in communication with an air quality monitor, such as a particle counter, and also in communication with a sensor having a variety of sensor settings, wherein the control system adjusts the sensor setting so that the fan speed is continuously, automatically and appropriately adjusted as the quality of the air changes. This would provide a more efficient cleaning filter and allow users within different countries, or within different geographical locations within the same country, to utilize all available fan speeds and all available sensor settings of the purifier.

SUMMARY OF THE INVENTION

In various embodiments, an air purifier of the present invention includes a particle counter that detects the amount of contaminants in the air, a control system programmed to receive input from the particle counter and continuously and automatically adjust the sensitivity setting of a sensor as the particle counter detects changes in the quality of air being purified, a sensor that controls the operation of a motorized fan as the sensitivity changes, and a motorized fan that responds to the instructions received through the sensor. In some embodiments, the sensor and the control system are combined into a single device. The particle counters continuously monitor the quality of the air passing through the air purifier. The control system is programmed so that the average air quality readings of the air leaving the sensor measured by the particle counters over a designated period of time fluctuate, the sensitivity of the sensor is automatically adjusted. The period of time could be set at a fixed period (e.g. 4 hours, 24 hours, etc.) or could be set to fluctuate (e.g. shorter periods during the day and longer periods during the night). The quality of air, measured by the average particulate readings, during the designated period of time will determine the sensitivity level of the sensor such that, if the air quality is poor (i.e. a high particulate count), then the sensitivity of the sensor will be adjusted to a less sensitive setting (i.e. it will allow higher fan speeds so that more air can be moved through the filter) if the air quality is good (i.e. a low particulate count), then the sensitivity of the sensor will be adjusted to a more sensitive setting (i.e. it will set a lower maximum fan speed because not as much air needs to move through the filter).

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

For a more complete understanding of the present invention and the advantages thereof, reference is now made to the following description taken in conjunction with the accompanying drawings in which like reference numerals indicate like features and wherein:

FIG. 1 is a chart showing an embodiment of the invention in which the control system adjusts the sensor sensitivity settings and fan speeds based on particle counts;

FIG. 4 is a table depicting how the control system can be programmed to adjust the sensor sensitivity level based on average particle count in one embodiment of the invention;

FIG. 5 is another representation of a table depicting how the control system can be programmed to adjust the sensor sensitivity level based on average particle count in the same embodiment of the invention;

DESCRIPTION OF THE PREFERRED EMBODIMENTS

Figure 2:
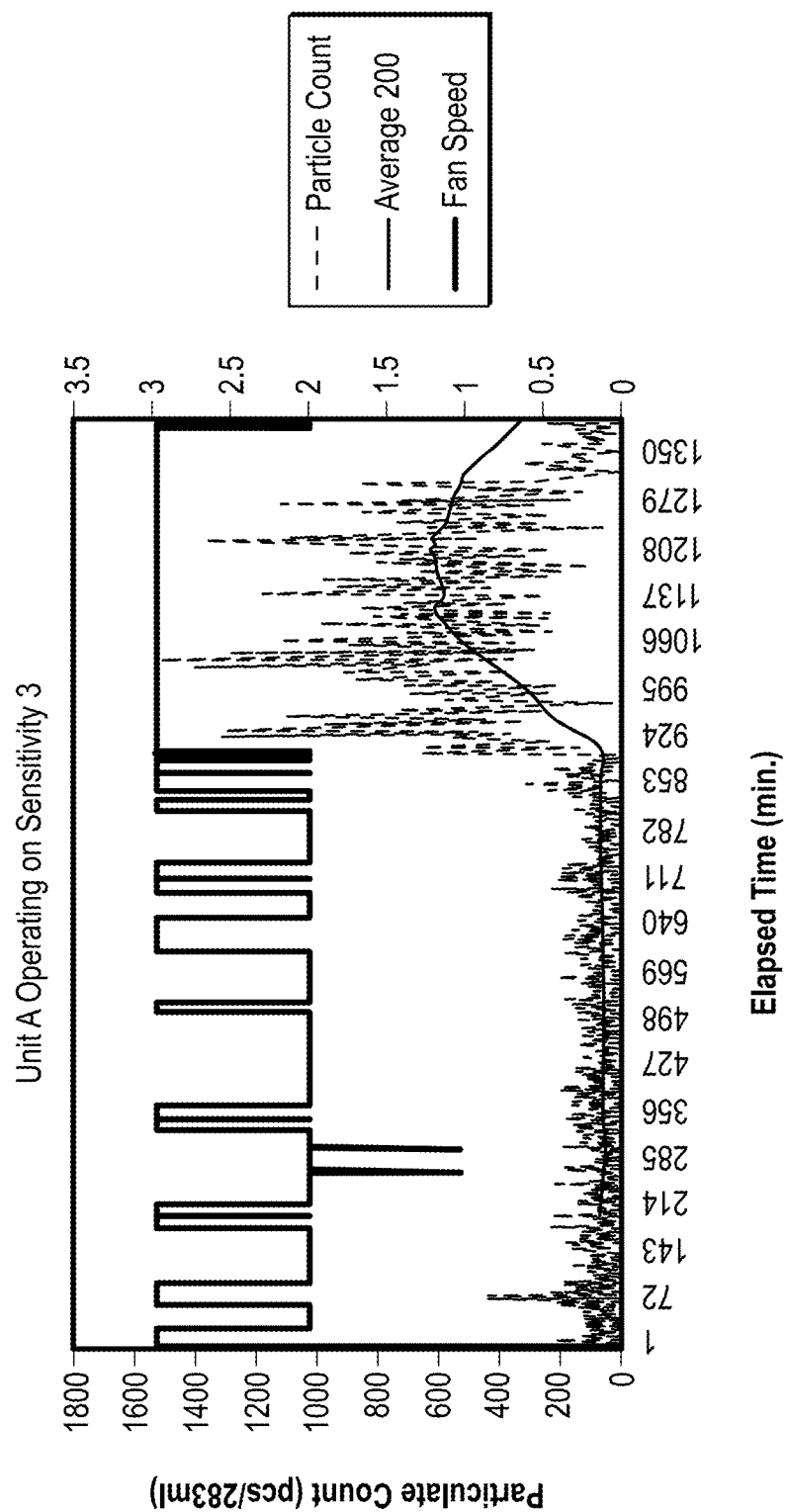
FIG. 2 is a graph showing the fan speed at different particle counts for an air purification unit when the control system designates sensor sensitivity 3.

The present invention is directed to improved methods and systems for, among other things, improving the performance of air purifiers. The configuration and use of the presently preferred embodiments are discussed in detail below. It should be appreciated, however, that the present invention provides many applicable inventive concepts that can be embodied in a wide variety of contexts other than the performance of air purifiers. Accordingly, the specific embodiments discussed are merely illustrative of specific ways to make and use the invention, and do not limit the scope of the invention.

The present invention relates to an air purifier in which a user desiring to remove particulates from the air in the room in which the purifier has been placed. Air purifiers known in the art typically have a number of different fan speed settings, with three to five settings being relatively common. The user would typically turn the unit on and set the fan speed to the desired setting. As the quality of the air changes, the user must adjust the fan speed to increase or decrease the flow of air through the filter.

The motorized fan induces air to flow into and through an air filter. As the speed of the fan increases, the amount of air passing through the filter also increases. As will be apparent to those skilled in the art, as the particulate matter in the air increases, it is necessary to increase the flow of air through the filter by increasing the speed of the fan.

Some air purifiers include a sensor that is programmed to increase or decrease the speed of the fan based on the amount of contaminants in the air. In those units, if amount of contaminant in the air is unacceptably high, the fan speed is increased and, if the amount of contaminant is acceptably low, the fan will run in low speed. In order to make the purifier as efficient as possible, the sensor should be correctly programmed so that it moves efficiently through the fan speed settings and doesn't, for example, constantly run on either a low setting or a high setting.

Referring now to FIG. 1 which shows the effect of a control system of one embodiment of the present invention programmed to control sensor sensitivity settings, and therefore fan speeds, based on particle counts. The control system in this embodiment is programmed to set seven different sensitivity settings. Setting 1 is the most sensitive of the seven settings. At that setting, if the particulate level is between 0 and 10 pcs/283 ml, the fan speed is set to "low;" if the particulate level is between 10 and 40 pcs/283 ml, the fan speed is set to "medium;" if the particulate level is between 40 and 100 pcs/283 ml, the fan speed is set to "high;" and if the particulate level is over 100 pcs/283 ml, the fan speed is set to "turbo."

When the control system adjusts the sensitivity of the sensor to setting 7, if the particulate level is between 0 and 1500 pcs/283 ml, the fan speed is set to "low;" if the particulate level is between 1500 and 2500 pcs/283 ml, the fan speed is set to "medium;" if the particulate level is between 2500 and 3000 pcs/283 ml, the fan speed is set to "high;" and if the particulate level is over 3000 pcs/283 ml, the fan speed is set to "turbo."

FIG. 2 shows a graph of one embodiment of an air purifier in which the control system has set the sensor sensitivity setting to 3, and the particulate count varying as the minutes elapse. As can be seen in the time period between 356 minutes and 853 minutes, the particulate count varies up to 200 pcs/283 ml, and the fan speed alternates efficiently between setting 2 (medium air flow) and setting 3 (high air flow). However, when the particulate count increases beginning around minute 924, the fan operates continuously at its highest setting which provides a poor user experience. The sensor may be set appropriately for the time period between 1 and 924 minutes, but is too sensitive (i.e. it considers all of the air to be "dirty" regardless of the particulate count) for the time period between 924 and 1350 minutes.

Figure 3:
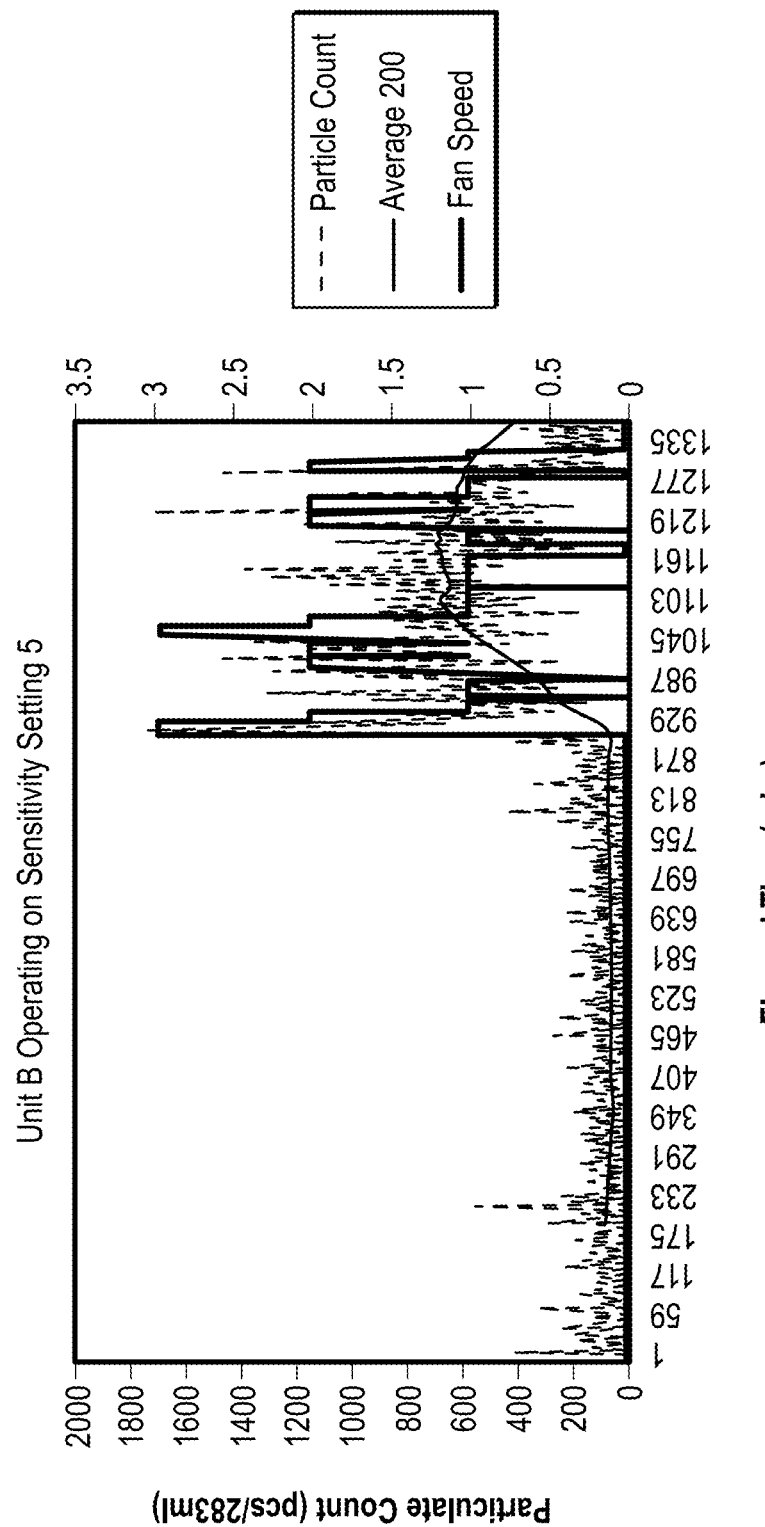
FIG. 3 is a graph showing the fan speed at different particle counts for an air purification unit when the control system designates sensor sensitivity 5.
Figure 6:
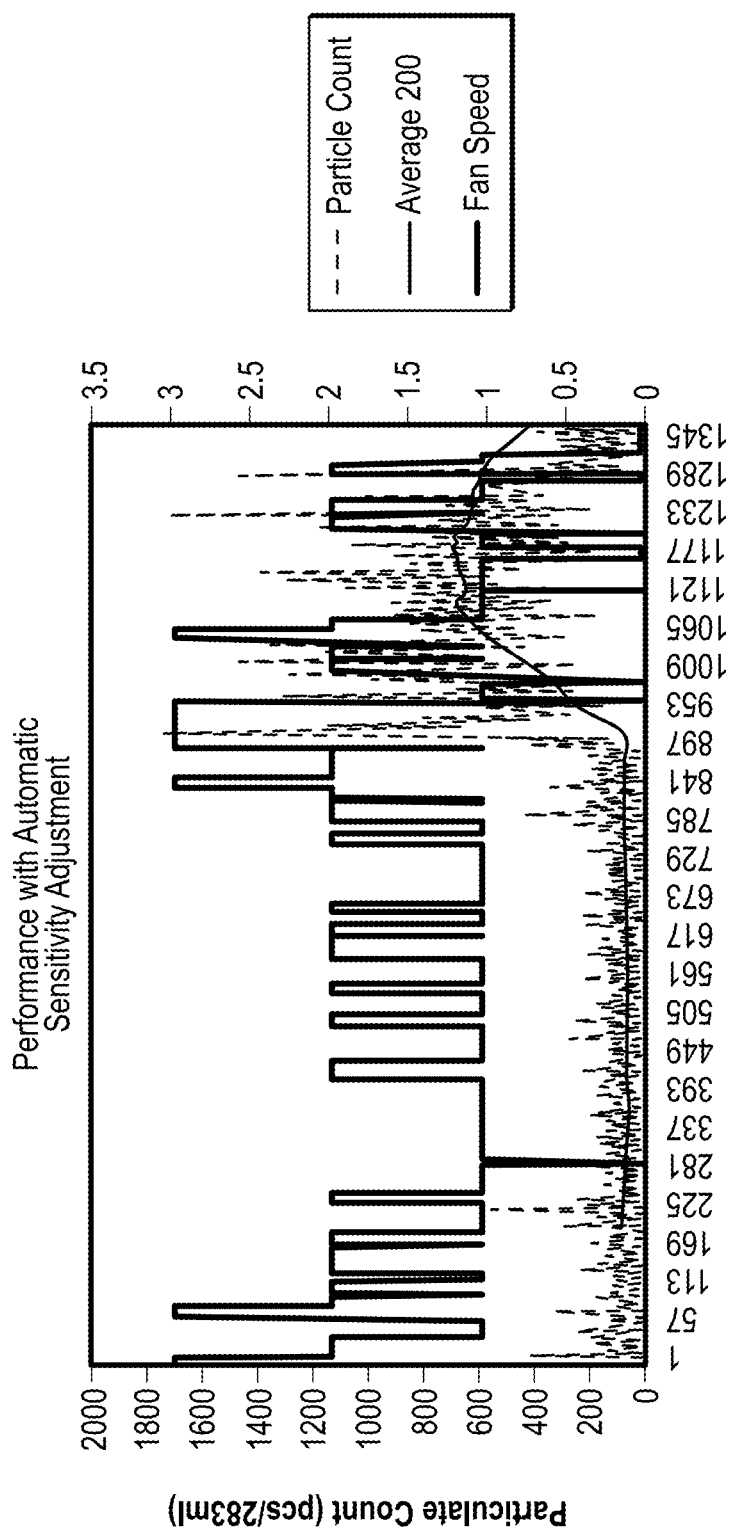
FIG. 6 is a graph showing the fan speed at different particle counts for an air purification unit with one embodiment of the automated sensitivity adjustment of the present invention.

FIG. 3 shows a graph of an embodiment of an air purifier in which the control system has set the sensor sensitivity to setting 5, and the particulate count varying as the minutes elapse. In this case, the fan is off or at the lowest setting (fan speed is 0) during the period of time between 1 and 929 minutes, even though the particulate count varies between 100 and 600 pcs/283 ml. After 929 minutes, the fan speed alternates between 0 and 3 as the particulate counts extends up to 1700 pcs/283 ml. The control system in this case is not sensitive enough (i.e. it considers all of the air to be "clean" regardless of the particulate count) for the range between 1 and 929 minutes, but may be set appropriately for the range between 929 and 1335 minutes.

In various embodiments of the present invention, the quality of the air passing through the air purifier is continuously monitored by the particle counter. The control system is programmed so that the average air quality readings of the air passing over the particle counter are monitored over a designated period of time and, as the average fluctuates, the sensitivity of the sensor is automatically adjusted. The period of time could be set at a fixed period (e.g. 4 hours, 24 hours, etc.) or could be set to fluctuate (e.g. shorter periods during the day and longer periods during the night). The quality of air, measured by the average particulate readings, during the designated period of time will determine the sensitivity level of the sensor such that, if the control system determines that the air quality is poor (i.e. a high particulate count), then it will adjust the sensitivity of the sensor to a less sensitive setting (i.e. it will allow higher fan speeds so that more air can be moved through the filter) if the control system determines that the air quality is good (i.e. a low particulate count), then it will adjust the sensitivity of the sensor to a more sensitive setting (i.e. it will set a lower maximum fan speed because not as much air needs to move through the filter).

For example, if the control system sets the sensor to a low sensitivity level the maximum fan speed available will be relatively low but, if the control system determines that the air passing over the particle detector as it leaves the unit is deteriorating (as determined by an increase in the average particle count over, for example, the prior four hours), the control system will adjust the sensitivity level of the sensor so that the maximum fan speed available increases.

In one embodiment of the present invention, the sensor is configured with seven settings corresponding to seven sensitivity tiers as shown in FIG. 4. The lowest sensitivity setting is configured to filter the cleanest air with particulate counts between 0 and 100 pcs/283 ml, the second lowest setting is configured to operate the fan at particulate counts between 30 and 250 pcs/283 ml, and so on up to the seventh sensitivity setting which is configured to adjust the fan speeds when particulate counts are between 1500 and 3000 pcs/283 ml. The control systems is programmed to continuously monitor the quality of the air as it passes over the particle counter and adjust the sensitivity setting of the sensor based on a moving average of the amount of particulate in the air.

In one embodiment of the present invention, the control system is programmed to adjust the sensor's sensitivity setting, and thereby adjust the available fan speeds, based on the moving average of amount of particulate over a period of time as shown in FIG. 5. In this case, if the average amount of particulate detected over a period of time is between 0 and 40 pcs/283 ml, the sensor will be set to sensitivity setting 1. Referring now back to FIG. 1, when the unit is set on sensitivity setting 1, the fan will operate at the low setting if the particulate count is between 0 and 10 pcs/283 ml, the fan will operate at the medium setting if the particulate count is between 10 and 40 pcs/283 ml, the fan will operate at the high setting if the particulate count is between 40 and 100 pcs/283 ml, and the fan will operate on the turbo setting if the particulate count is over 100 pcs/283 ml.

The control system will continue to monitor the quality of the air passing over the particle counter. If the average amount of particulate over a period of time is no longer between 0 and 40 pcs/283 ml, it will adjust the sensitivity setting. For example, if the average amount of particulate over a period of time changes to between 100 and 250 pcs/283 ml, the control system will adjust the sensitivity setting of the unit to sensitivity level 3, as shown in FIG. 5. This will cause the fan to operate at the low setting if the particulate count is between 0 and 100 pcs/283 ml, at the medium setting if the particulate count is between 100 and 250 pcs/283 ml, at the high setting if the particulate count is between 250 and 750 pcs/283 ml, and on the turbo setting if the particle count is over 750 pcs/283 ml. The sensor will then continue to monitor the air leaving the unit and will continue to make adjustments as necessary based on the average particle count leaving the unit.

One advantage of the present invention is an improved user experience. If a sensor is not able to adjust to different sensitivity levels, it could remain in the wrong setting for an indefinite period of time. For example, if a unit is configured with one sensitivity setting that is intended to perform optimally when particulate levels are between 0 and 750 pcs/283 ml, the unit will operate continuously when the air quality is above 750 pcs/283 ml. In those instances in which this unit is shipped to a region with a poor air quality, or is shipped to a region with a good air quality but that air quality deteriorates for some reason, the unit will continue to operate on the "Turbo" setting and will not cycle through its normal range of "low," "medium," "high," and "turbo." This generates unnecessary noise for the user and unneeded wear and tear on the unit.

Referring now to FIG. 7 which shows a graph of one embodiment of an air purifier of the present invention in which the control system has initially set the sensor to setting 2, and the particulate count varying as the minutes elapse. As can be seen in the range between 1 minute and 897 minutes, the particulate count varies up to 200 pcs/283 ml, and the fan speed alternates between off and setting 3 (high air flow). At sensitivity setting 2, the air flow at the high setting is 250 cfm.

The average particle count increases shortly after 897 minutes and spikes to nearly 1800 pcs/283 ml. When the particulate count increases, the fan initially operates continuously at its highest setting. The control systems detects the increase in the average particle count and adjusts the sensitivity setting of the sensor from setting 2 to setting 5. At a sensitivity setting of 5, the highest fan speed is 1,250 cfm. The higher fan speed enables the unit to move more of the air through the filter, thereby more quickly and efficiently cleaning the air.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of air purification units known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

What is claimed is:

1. A method for purifying air, comprising:
passing air over a particle counter in communication with a control system;
determining through the control system an initial level of air quality based on a particle count detected by the particle counter;
designating a first sensitivity setting of a sensor in communication with the control system and further in communication with a fan, wherein the first sensitivity setting allows the fan to generate a first set of airflows;
determining through the control system a second level of air quality based on a second particle count detected by the particle counter;
if the second level of air quality deviates from the initial level of air quality by more than a specified amount, adjusting the first sensitivity setting of the sensor to a second sensitivity setting, thereby allowing the fan to generate a second set of airflows.

2. The method of claim 1, wherein the second level of air quality is determined after a pre-specified period of time.

3. The method of claim 1, wherein if the second level of air quality contains more particulate than the initial level of air quality, the second set of airflows is greater than the first set of airflows.

4. The method of claim 1, wherein if the second level of air quality contains fewer particulate than the initial level of air quality, the second set of airflows is less than the first set of airflows.

5. The method of claim 1, further including an indicator that provides a visual indication of the first set of airflows.

6. The method of claim 1, wherein the control system is an integral part of the sensor.

7. An air purifier, comprising:
a control system in communication with a particle counter and in further communication with a sensor controlling a fan moving air through a filter; wherein the sensor is configured to adjust between tiers of fan speed sensitivity settings;
wherein the control system determines an initial level of air quality based on the particle count detected by the particle counter and designates a first sensitivity setting of the sensor thereby allowing the fan to generate a first set of airflows;
wherein the control system subsequently determines a second level of air quality based on the particle count detected by the particle counter and designates a second sensitivity setting of the sensor; and
if the second level of air quality deviates from the initial level of air quality by more than a specified amount, adjusting a sensitivity setting of the sensor through the control system, thereby allowing the fan to generate a second set of airflows.

8. The air purifier of claim 7, wherein the second level of air quality is determined after a pre-specified period of time.

9. The air purifier of claim 7, wherein if the second level of air quality contains more particulate than the initial level of air quality, the second set of airflows are greater than the initial set of airflows.

10. The air purifier of claim 7, wherein if the second level of air quality contains fewer particulate than the initial level of air quality, the second set of airflows are lower than the initial set of airflows.

11. The air purifier of claim 7, further including an indicator that provides a visual indication of the first set of airflows.

12. The air purifier of claim 7, wherein the control system is an integral part of the sensor.

* * * * *